(12) United States Patent
Ohashi et al.

(10) Patent No.: US 6,297,244 B1
(45) Date of Patent: Oct. 2, 2001

(54) STABLE DRUG COMPOSITION

(75) Inventors: Mamoru Ohashi, Amagasaki; Kazuyoshi Ogasawara, Nara-ken; Yoshimi Shirai, Suita; Hiroshi Fujioka, Ibaraki, all of (JP)

(73) Assignee: Dainippon Pharmaceutical Co., Ltd., Osaka-fu (JP)

( * ) Notice: Subject to any disclaimer, the term of this patent is extended or adjusted under 35 U.S.C. 154(b) by 0 days.

(21) Appl. No.: 09/529,719

(22) PCT Filed: Oct. 15, 1998

(86) PCT No.: PCT/JP98/04657
§ 371 Date: Apr. 19, 2000
§ 102(e) Date: Apr. 19, 2000

(87) PCT Pub. No.: WO99/20276
PCT Pub. Date: Apr. 29, 1999

(30) Foreign Application Priority Data

Oct. 20, 1997 (JP) .................................. 9-306634

(51) Int. Cl.$^7$ .................................. A61K 31/50
(52) U.S. Cl. .................................. 514/249
(58) Field of Search .................................. 514/249

(56) References Cited

U.S. PATENT DOCUMENTS 5,258,382 * 11/1993 Negoro et al. .................. 514/249

FOREIGN PATENT DOCUMENTS 5-186472  4/1996 (JP) .

OTHER PUBLICATIONS

Osol et al., Editor–in–Chief, Remington's Pharmaceutical Sciences, copyright Jun. 11, 1976.*
English Language Translation of the Material Portion of the Document:"Practical Drug Additives (In Japanese)", edited by Research Team Concerning Drug Additives, Mar. 5, 1974, pp. 215–217, 258–259 (cited in the International Search Report of the original PCT/JP98/04657).
Chemical Abstracts, 122, 9860 (1995) (English Abstract of JP–A–6–192222).
Chemical Abstracts, 125, 221569 (1996) (English Abstract of JP–A–8–176105).
"Practical Drug Additives (In Japanese)", edited by Research Team Concerning Drug Additives, Mar. 5, 1974, pp. 215–217, 258–259.

* cited by examiner

Primary Examiner—Dwayne C. Jones
(74) Attorney, Agent, or Firm—Wenderoth, Lind & Ponack, L.L.P.

(57) ABSTRACT

A stabilized pharmaceutical composition comprising (R)-2-(4-bromo-2-fluorobenzyl)-1,2,3,4-tetrahydropyrrolo[1,2-a]pyrazine-4-spiro-3'-pyrrolidine-1,2',3,5'-tetrone (hereinafter, referred to as "AS-3201") and as a stabilizer at least one acidic substance having an acidity more potent than that of AS-3201, such as ascorbic acid, citric acid, tartaric acid, lactic acid, maleic acid, malic acid or phosphoric acid.

18 Claims, No Drawings

STABLE DRUG COMPOSITION

BACKGROUND OF THE INVENTION

1. Field of the Invention

The present invention relates to a stabilized pharmaceutical composition of (R)-2-(4-bromo-2-fluorobenzyl)-1,2,3,4-tetrahydropyrrolo[1,2-a]pyrazine-4-spiro-3'-pyrrolidine-1,2',3,5'-tetrone (hereinafter, referred to as "AS-3201") having a potent aldose reductase inhibitory activity.

2. Description of Related Art

AS-3201 is the compound of the following formula. Said compound is described in Example 22 of Japanese Patent No. 2516147 (U.S. Pat. No. 5,258,382), Reference Example 12 of JP-A-6-192222 (Chem. Abstr., 122, 9860 (1995)), and Experiment of JP-A-8-176105 (Chem. Abstr., 125, 221569 (1996)), and its potent aldose reductase inhibitory activities are disclosed therein.

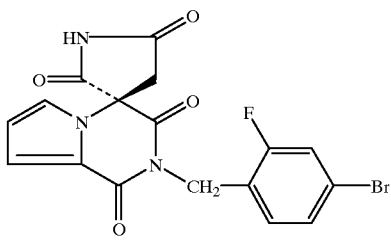

Example 28 of Japanese Patent No. 2516147 (U.S. Pat. No. 5,258,382) describes a method for preparing specific tablets of AS-3201. That is, it is described therein that AS-3201 (1 g), corn starch (25 g), lactose (58 g), crystalline cellulose (11 g), hydroxypropylcellulose (3 g), light anhydrous silicic acid (1 g) and magnesium stearate (1 g) are blended, granulated and made into 1,000 tablets each weighing 100 mg by a conventional method.

During the studies on methods for preparing AS-3201-containing pharmaceutical compositions having a good stability on store, the present inventors have found that AS-3201 drug substance per se is stable against heat and humidity, but when AS-3201 is mixed with pharmaceutical excipients or carriers, AS-3201 shows a tendency of increasing its degradation product at a higher temperature under higher humidity.

Under such circumstances, the present inventors have further intensively studied, and have found that the stability of AS-3201-containing pharmaceutical compositions is remarkably improved by adding thereto as a stabilizer at least one acidic substance having an acidity more potent than that of AS-3201, and finally have accomplished the present invention.

SUMMARY OF THE INVENTION

The present invention provides an AS-3201-containing pharmaceutical composition which comprises as a stabilizer at least one acidic substance having an acidity more potent than that of AS-3201.

In the present specification, the term "$pK_{a1}$" means an acid dissociation exponent of an acidic substance at 25° C. in an infinitely diluted solution thereof. When an acidic substance is a polybasic acid, it means an acid dissociation exponent at the first step of dissociation. The term "water-solubility" means a maximum amount of a solute being dissolved in 100 ml of water. The term "about" is used with the intention of including values following said term.

The stabilizer for the pharmaceutical composition of the present invention includes any pharmaceutically acceptable acidic substances having an acidity more potent than that of AS-3201, i.e., $pK_a$=5.6–5.8. Examples of those substances are adipic acid, ascorbic acid, aspartic acid, glutamic acid, citric acid, succinic acid, tartaric acid, lactic acid, fumaric acid, maleic acid, malic acid, and phosphoric acid. In addition, acidic substances having a $pK_{a1}$ of less than about 4.5 and a water-solubility at 15° C. to 25° C. of larger than about 10 g/100 ml are preferable. Preferable acidic substances are, for example, ascorbic acid, citric acid, tartaric acid, lactic acid, maleic acid, malic acid and phosphoric acid. Especially preferable acidic substances are one having a $pK_{a1}$ of less than about 3.3 and a water-solubility at 15° C. to 25° C. of larger than about 50 g/100 ml, and include, for example, citric acid, tartaric acid, maleic acid and phosphoric acid, and among these acids, tartaric acid is most preferable.

The content of the acidic substances may vary depending on the acidity or water-solubility of such substances and the kinds of pharmaceutical excipients or carriers to be combined, but it is usually in the range of about 0.2% by weight to about 10% by weight to the total weight of the pharmaceutical composition, more preferably in the range of about 0.5% by weight to about 2.5% by weight. The acidic substance is added alone or in a mixture of two or more substances.

The pharmaceutical composition of the present invention may be solid dosage forms, and includes, for example, tablets, capsules, granules, powders, etc. These pharmaceutical compositions can be prepared by mixing AS-3201 with pharmaceutical excipients or carriers such as diluents, disintegrators, binders and lubricants and an acidic substance as a stabilizer by a conventional method. The acidic substances may be added per se or in the form of a solution thereof in water or other suitable solvent which is used in the preparation procedure of the pharmaceutical composition, depending on the method of preparing the composition. The pharmaceutical composition of the present invention may optionally be coated, or may additionally contain surfactants, coloring agents, flavoring agents, etc.

The pharmaceutical excipients or carriers may be any ones except for ones showing a bad compatibility with AS-3201. The diluents include, for example, lactose, starch, crystalline cellulose, D-mannitol, sucrose, glucose, erythritol, xylitol, D-sorbitol, anhydrous dibasic calcium phosphate, and calcium sulfate. The disintegrators are, for example, starch, crystalline cellulose, low substituted hydroxypropylcellulose, carmellose, carmellose calcium, sodium carboxymethyl starch, croscarmellose sodium, partly pregelatinized starch, and hydroxypropyl starch. The binders are, for example, acacia, starch, hydroxypropylcellulose, hydroxypropylmethylcellulose, polyvinyl alcohol, pullulan, gelatin, ethylcellulose, methylcellulose, carmellose sodium, and dextrin. The lubricants are, for example, magnesium stearate, calcium stearate, stearic acid, sucrose esters of fatty acids, light anhydrous silicic acid, talc, hydrogenated oil, and macrogol.

The surfactants to be used in the present pharmaceutical composition are, for example, sorbitan fatty acid esters and polysorbates. The coloring agents are, for example, tar color, caramel, and red iron oxide. The flavoring agents are, for example, sweeteners and perfumes.

The content of AS-3201 in the pharmaceutical composition of the present invention is usually in the range of about 0.5% by weight to about 25% by weight to the total weight of the pharmaceutical composition. The acidic substance as a stabilizer is especially effective for improving stability of a pharmaceutical composition wherein the content of AS-3201 is comparatively low. In order to store the AS-3201-containing pharmaceutical composition of the present invention more stably, the present composition may be packed in a bottle using materials of low moisture-permeability or in damp-proof packages such as heat-sealed packages, if necessary.

DETAILED DESCRIPTION OF THE INVENTION

The present invention is illustrated in more detail by Examples and Comparative Examples, but the present invention should not be construed to be limited thereto. Incidentally, AS-3201 was used after being micronized.

In Examples and Comparative Examples, the amount of degradation products of the AS-3201-containing pharmaceutical compositions was assayed by High Performance Liquid Chromatography (HPLC). A test sample was dissolved or dispersed in acetonitrile, and the solution in an amount corresponding to 2 μg of AS-3201 was charged to an HPLC column. The conditions for assay are as follows.

Column: Develosil ODS-5 (manufactured by Nomura Chemical Co., Ltd., Japan) (Φ 5 mm×150 mm)

Column temperature: 40° C.

Mobile phase: a mixture of 0.1 M phosphate buffer (pH 3.3)/acetonitrile/tetrahydrofuran (3:1:1)

Flow rate: 1.0 ml/min.

Wavelength: ultraviolet absorption at 220 nm

Based on the assay results, the degradation percentage of AS-3201 was calculated by the following equation.

$$\text{Degradation Percentage} = \frac{\text{Area (Total)} - \text{Area } (AS\text{-}3201)}{\text{Area (Total)}}$$

Area (Total): Area of total peaks (retention time: 2–30 min.)

Area (AS-3201): Area of the peak of AS-3201 (retention time: about 10 min.)

EXAMPLE 1 AND COMPARATIVE EXAMPLE 1

Preparation of Tablets

|  | Ex. 1 | Comparative Ex. 1 |
| --- | --- | --- |
| AS-3201 | 10 g | 10 g |
| Tartaric acid | 10 g | — |
| Lactose | 740 g | 750 g |
| Corn starch | 200 g | 200 g |
| Polyvinyl alcohol | 20 g | 20 g |
| Magnesium stearate | 20 g | 20 g |
| Total | 1000 g | 1000 g |

AS-3201, lactose and corn starch were charged in a high-shear granulator, and the mixture was granulated with a solution of tartaric acid in a 10% aqueous polyvinyl alcohol solution. The granules were dried, and thereto was added magnesium stearate, and the resultant was blended in a V-blender. The mixture was compressed on a rotary tableting machine to give tablets weighing 100 mg and containing 1 mg of AS-3201 each.

In Comparative Example 1, tablets wherein the tartaric acid in the above Example's formulation was replaced by the same amount of lactose were prepared in the same manner and compared.

The tablets of Example 1 and Comparative Example 1 were put into a glass bottle, and the bottle was stored with being sealed by stopper at 50° C. for one month or without stopper at 50° C.—75% relative humidity (RH) for one month. The amount of degradation products of AS-3201 was assayed and the degradation percentage was calculated. The results are shown in Table 1.

TABLE 1

|  | Degradation Percentage of AS-3201 | |
| --- | --- | --- |
| Condition for storage | Ex. 1 | Comp. Ex. 1 |
| sealed with stopper, 50° C., one month | 0.6% | 3.8% |
| without stopper, 50° C.-75% RH, one month | 0.8% | 14.1% |

EXAMPLE 2 AND COMPARATIVE EXAMPLE 2

Preparation of Tablets

|  | Ex. 2 | Comparative Ex. 2 |
| --- | --- | --- |
| AS-3201 | 1 g | 1 g |
| Fumaric acid | 5 g | — |
| D-Mannitol | 70 g | 75 g |
| Carboxymethyl starch sodium | 20 g | 20 g |
| Hydroxypropylcellulose | 2 g | 2 g |
| Magnesium stearate | 2 g | 2 g |
| Total | 100 g | 100 g |

AS-3201, fumaric acid, D-mannitol, carboxymethyl starch sodium and hydroxypropylcellulose were mixed in a V-blender, and thereto was added magnesium stearate, and the resultant was mixed. The mixture was compressed on a single-punch tableting machine to give tablets weighing 100 mg and containing 1 mg of AS-3201 each.

In Comparative Example 2, tablets wherein the fumaric acid in the above Example's formulation was replaced by the same amount of D-mannitol were prepared, and compared.

The tablets of Example 2 and Comparative Example 2 were put into a glass bottle, and the bottle was stored with being sealed by stopper at 50° C. for one month or without stopper at 50° C.—75% RH for one month. The amount of degradation products of AS-3201 was assayed and the degradation percentage was calculated. The results are shown in Table 2.

TABLE 2

| Condition for storage | Degradation Percentage of AS-3201 | |
| --- | --- | --- |
| | Ex. 2 | Comp. Ex. 2 |
| sealed with stopper, 50° C., one month | 1.6% | 6.4% |
| without stopper, 50° C.-75% RH, one month | 9.0% | 27.0% |

EXAMPLE 3 AND COMPARATIVE EXAMPLE 3

Preparation of Capsules

| | Ex. 3 | Comparative Ex. 3 |
| --- | --- | --- |
| AS-3201 | 1 g | 1 g |
| Lactic acid | 1 g | — |
| Lactose (for direct tableting) | 75 g | 76 g |
| Carmellose calcium | 20 g | 20 g |
| Hydroxypropylmethylcellulose 2910 | 2 g | 2 g |
| Magnesium stearate | 1 g | 1 g |
| Total | 100 g | 100 g |

AS-3201, carmellose calcium and lactic acid were mixed well in a mortar, and the mixture was screened through a 30 mesh sieve. To the mixture were added lactose and hydroxypropylmethylcellulose 2910, and the resulting mixture was blended in a V-blender. To the resultant was added magnesium stearate, and the mixture was further mixed. The mixture was filled into a No. 3 capsule in an amount of 180 mg per capsule to give capsules containing 1.8 mg of AS-3201 each.

In Comparative Example 3, capsules wherein the lactic acid in the above Example's formulation was replaced by the same amount of lactose were prepared, and compared.

The capsules of Example 3 and Comparative Example 3 were put into a glass bottle, and the bottle was stored with being sealed by stopper at 50° C. for one month or without stopper at 50° C.—75% RH for one month. The amount of degradation products of AS-3201 was assayed and the degradation percentage was calculated. The results are shown in Table 3.

TABLE 3

| Condition for storage | Degradation Percentage of AS-3201 | |
| --- | --- | --- |
| | Ex. 3 | Comp. Ex. 3 |
| sealed with stopper, 50° C., one month | 0.8% | 2.0% |
| without stopper, 50° C.-75% (RH), one month | 1.0% | 4.7% |

EXAMPLE 4 AND COMPARATIVE EXAMPLE 4

Preparation of Powders

| | Ex. 4 | Comparative Ex. 4 |
| --- | --- | --- |
| AS-3201 | 10 g | 10 g |
| Citric acid | 30 g | — |
| Lactose | 740 g | 770 g |
| Low substituted hydroxypropylcellulose | 200 g | 200 g |
| Hydroxypropylcellulose | 20 g | 20 g |
| Total | 1000 g | 1000 g |

AS-3201, lactose and low substituted hydroxypropylcellulose were charged into a fluid bed granulator and drier, and the mixture was granulated by spraying thereto a solution of citric acid in a 5% aqueous hydroxypropylcellulose solution. After drying, the resultant was screened through a 30 mesh sieve to give 1% AS-3201-containing powders.

In Comparative Example 4, powders wherein the citric acid in the above Example's formulation was replaced by the same amount of lactose were prepared, and compared.

The powders of Example 4 and Comparative Example 4 were put into a glass bottle, and the bottles were stored with being sealed by stopper at 50° C. for one month or without stopper at 50° C.—75% RH for one month. The amount of degradation products of AS-3201 was assayed and the degradation percentage was calculated. The results are shown in Table 4.

TABLE 4

| Condition for storage | Degradation percentage of AS-3201 | |
| --- | --- | --- |
| | Ex. 4 | Comp. Ex. 4 |
| sealed with stopper, 50° C., one month | 0.1% | 4.8% |
| without stopper, 50° C.-75% RH, one month | 1.3% | 19.8% |

EXAMPLE 5 AND COMPARATIVE EXAMPLE 5

Preparation of Tablets

| | Ex. 5 | Comparative Ex. 5 |
| --- | --- | --- |
| AS-3201 | 10 g | 10 g |
| Phosphoric acid | 10 g | — |
| Lactose | 740 g | 750 g |
| Low substituted hydroxypropylcellulose | 200 g | 200 g |
| Hydroxypropylcellulose | 20 g | 20 g |
| Magnesium stearate | 20 g | 20 g |
| Total | 1000 g | 1000 g |

AS-3201, lactose and low substituted hydroxypropylcellulose were charged in a fluid bed granulator and drier, and the mixture was granulated by spraying thereto a solution of phosphoric acid in a 5% aqueous hydroxypropylcellulose solution. The granules were dried, and thereto was added magnesium stearate, and the resultant was blended in a V-blender. The mixture was compressed on a rotary tableting machine to give tablets weighing 100 mg and containing 1 mg of AS-3201 each.

In Comparative Example 5, tablets wherein the phosphoric acid in the above Example's formulation was replaced by the same amount of lactose were prepared, and compared.

The tablets of Example 5 and Comparative Example 5 were put into a glass bottle, and the bottle was stored with being sealed by stopper at 50° C. for one month or without stopper at 50° C.—75% RH for one month. The amount of degradation products of AS-3201 was assayed and the degradation percentage was calculated. The results are shown in Table 5.

TABLE 5

| Condition for storage | Degradation Percentage of AS-3201 | |
|---|---|---|
| | Ex. 5 | Comp. Ex. 5 |
| sealed with stopper, 50° C., one month | 0.1% | 4.8% |
| without stopper, 50° C.-75% RH, one month | 0.5% | 19.8% |

EXAMPLE 6

Preparation of Tablets

| AS-3201 | 20 g |
|---|---|
| Tartaric acid | 8 g |
| Lactose | 732 g |
| Low substituted hydroxypropylcellulose | 200 g |
| Hydroxypropylcellulose | 20 g |
| Magnesium stearate | 20 g |
| Total | 1000 g |

AS-3201 was micronized using a Single Truck Jet Mill (manufactured by SEISHIN ENTERPRISE Co., LTD.) with compression air pressure of 6 kgf/cm$^2$, and the micronized AS-3201 was charged into a fluid bed granulator and drier together with lactose and low substituted hydroxypropylcellulose. The mixture was granulated by spraying thereto a solution of tartaric acid in a 5% aqueous hydroxypropylcellulose solution. The granules were dried, and thereto was added magnesium stearate, and the resultant was blended in a V-blender. The mixture was compressed on a rotary tableting machine to give tablets weighing 125 mg and containing 2.5 mg of AS-3201 each.

After storing the tablets thus obtained with being sealed by stopper or without stopper at 50° C.—75% RH for one month, the degradation percentages were 0.1% and 0.8% respectively.

EXAMPLE 7

Preparation of Tablets

| AS-3201 | 160 g |
|---|---|
| Tartaric acid | 8 g |
| Lactose | 492 g |
| Low substituted hydroxypropylcellulose | 300 g |
| Hydroxypropylcellulose | 20 g |
| Magnesium stearate | 20 g |
| Total | 1000 g |

In the same manner as in Example 6, the tablets weighing 125 mg and containing 20 mg of AS-3201 each were prepared. After storing the tablets thus obtained with being sealed by stopper or without stopper at 50° C.—75% RH for one month, the degradation percentages were 0.1% and 0.2% respectively.

INDUSTRIAL APPLICABILITY

As explained above, the AS-3201-containing pharmaceutical composition of the present invention shows an excellent stability. Especially, the stability is remarkably improved in the pharmaceutical compositions containing AS-3201 in a low amount.

What is claimed is:

1. A pharmaceutical composition comprising as an active ingredient (R)-2-(4-bromo-2-fluorobenzyl)-1,2,3,4-tetrahydropyrrolo[1,2-a]pyrazine-4-spiro-3'-pyrrolidine-1,2',3,5'-tetrone and as a stabilizer at least one acidic substance having an acidity more potent than that of the said active ingredient.

2. The pharmaceutical composition according to claim 1, wherein the stabilizer is an acidic substance having a pK$_{a1}$ of less than about 4.5 and a water-solubility at 15° C. to 25° C. of larger than about 10 g/100 ml.

3. The pharmaceutical composition according to claim 2, wherein the stabilizer is an acidic substance having a pK$_{a1}$ of less than about 3.3 and a water-solubility at 15° C. to 25° C. of larger than about 50 g/100 ml.

4. The pharmaceutical composition according to claim 2, wherein the acidic substance is one or more members selected from the group consisting of ascorbic acid, citric acid, tartaric acid, lactic acid, maleic acid, malic acid and phosphoric acid.

5. The pharmaceutical composition according to claim 3, wherein the acidic substance is one or more members selected from the group consisting of citric acid, maleic acid, and phosphoric acid.

6. The pharmaceutical composition according to claim 3, wherein the acidic substance is tartaric acid.

7. The pharmaceutical composition according to claim 1, wherein the content of the acidic substance is in the range of about 0.2% by weight to about 10% by weight to the total weight of the pharmaceutical composition.

8. The pharmaceutical composition according to claim 2, wherein the content of the acidic substance is in the range of about 0.2% by weight to about 10% by weight to the total weight of the pharmaceutical composition.

9. The pharmaceutical composition according to claim 3, wherein the content of the acidic substance is in the range of about 0.2% by weight to about 10% by weight to the total weight of the pharmaceutical composition.

10. The pharmaceutical composition according to claim 4, wherein the content of the acidic substance is in the range of about 0.2% by weight to about 10% by weight to the total weight of the pharmaceutical composition.

11. The pharmaceutical composition according to claim 5, wherein the content of the acidic substance is in the range of about 0.2% by weight to about 10% by weight to the total weight of the pharmaceutical composition.

12. The pharmaceutical composition according to claim 6, wherein the content of the acidic substance is in the range of about 0.2% by weight to about 10% by weight to the total weight of the pharmaceutical composition.

13. The pharmaceutical composition according to claim 7, wherein the content of the acidic substance is in the range of about 0.5% by weight to about 2.5% by weight.

14. The pharmaceutical composition according to claim 8, wherein the content of the acidic substance is in the range of about 0.5% by weight to about 2.5% by weight.

15. The pharmaceutical composition according to claim 9, wherein the content of the acidic substance is in the range of about 0.5% by weight to about 2.5% by weight.

16. The pharmaceutical composition according to claim 10, wherein the content of the acidic substance is in the range of about 0.5% by weight to about 2.5% by weight.

17. The pharmaceutical composition according to claim 11, wherein the content of the acidic substance is in the range of about 0.5% by weight to about 2.5% by weight.

18. The pharmaceutical composition according to claim 12, wherein the content of the acidic substance is in the range of about 0.5% by weight to about 2.5% by weight.

* * * * *